US00PP36038P3

(12) United States Plant Patent
Olesen

(10) Patent No.: US PP36,038 P3
(45) Date of Patent: Jul. 30, 2024

(54) SHRUB ROSE PLANT NAMED 'POULREN041'

(50) Latin Name: *Rosa hybrida*
Varietal Denomination: Poulren041

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 24 days.

(21) Appl. No.: 17/803,619

(22) Filed: Sep. 13, 2022

(65) Prior Publication Data

US 2024/0090356 P1 Mar. 14, 2024

(30) Foreign Application Priority Data

Sep. 24, 2021 (QZ) ..... PBR 2021/2352

(51) Int. Cl.
*A01H 5/02* (2018.01)
*A01H 6/74* (2018.01)

(52) U.S. Cl.
USPC ..... Plt./102
CPC ..... *A01H 6/749* (2018.05); *A01H 5/02* (2013.01)

(58) Field of Classification Search
USPC ..... Plt./102, 107, 141, 148, 149
CPC . A01H 5/02; A01H 5/00; A01H 6/749; A01H 6/74
See application file for complete search history.

(56) References Cited

PUBLICATIONS

Floraland 2020 retrieved on Dec. 4, 2023 at https://floraland.ro/wp-content/uploads/2021/08/Floraland-Trandafir-si-clematis_2021.pdf, 3 pp. (Year: 2022).*

* cited by examiner

*Primary Examiner* — June Hwu

(57) ABSTRACT

A new garden rose plant of the Shrub class which has abundant, pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulren041'.

This application claims priority to Plant Breeder's Rights Application Number 2021/2352, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren041', originated as a single seedling from the stated cross.

The new variety may be distinguished from its male pollen parent and female seed parent primarily by the following characteristics. The male pollen parent plant has red flowers while the new variety has pink flowers. The female seed parent plant has red flowers while the new variety has pink flowers.

The objective of the hybridization of this rose variety was to create a new and distinct variety with unique qualities, such as:

1. Uniform and abundant pink, perfumed flowers;
2. Vigorous, but compact growth when propagated on its own roots;
3. Exceptional disease resistance.

This combination of qualities is not present in previously available commercial cultivars of this type, known to the inventor, and distinguish 'Poulren041' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren041' was selected in the spring of 2014 by the inventor as a single plant from the progeny of the aforementioned hybridization.

Asexual reproduction of 'Poulren041' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren041' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren041'.

Specifically illustrated in FIG. 1 of the drawings are mature and juvenile leaves, and bare stems.

Figure 1:
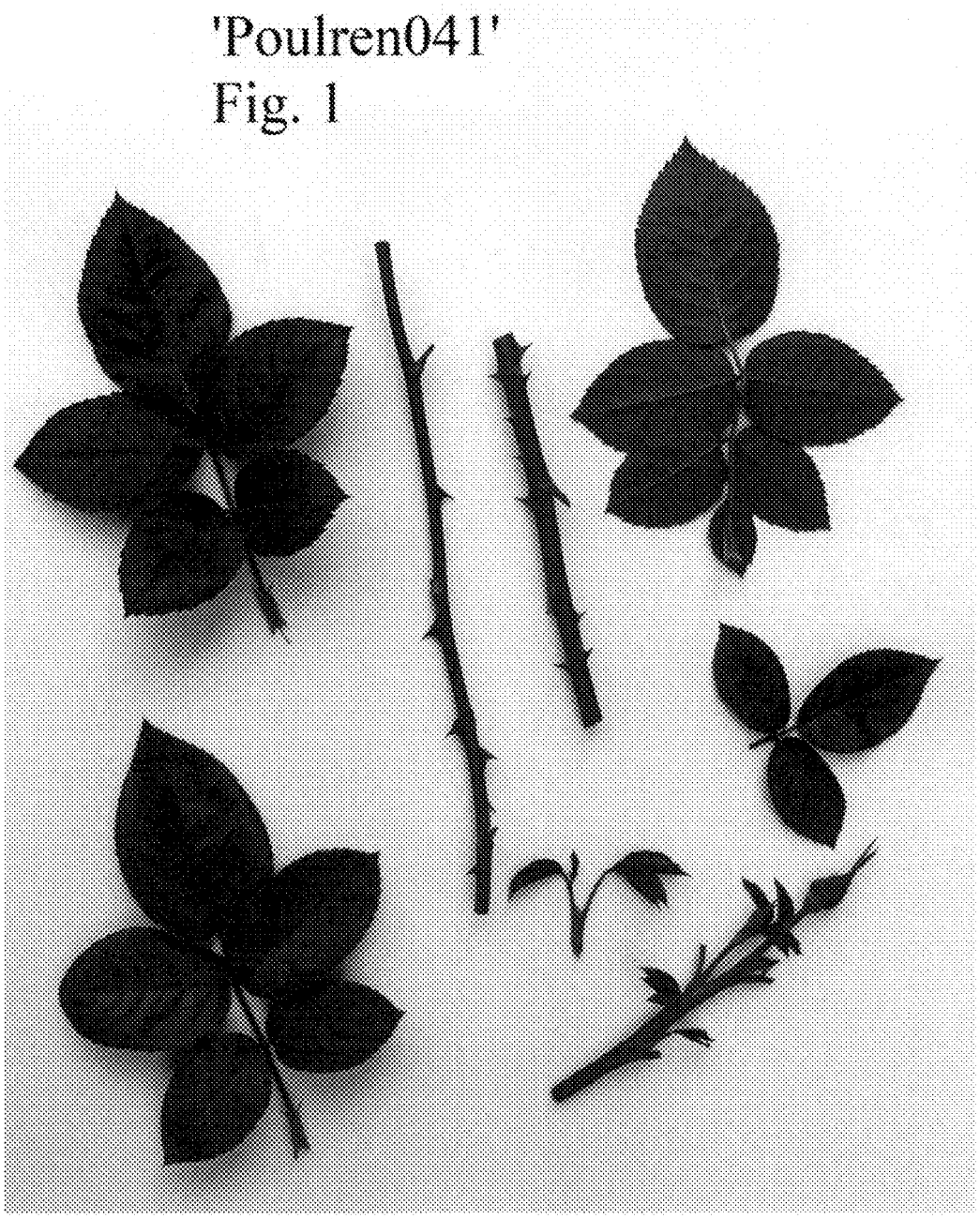
Figure 2:
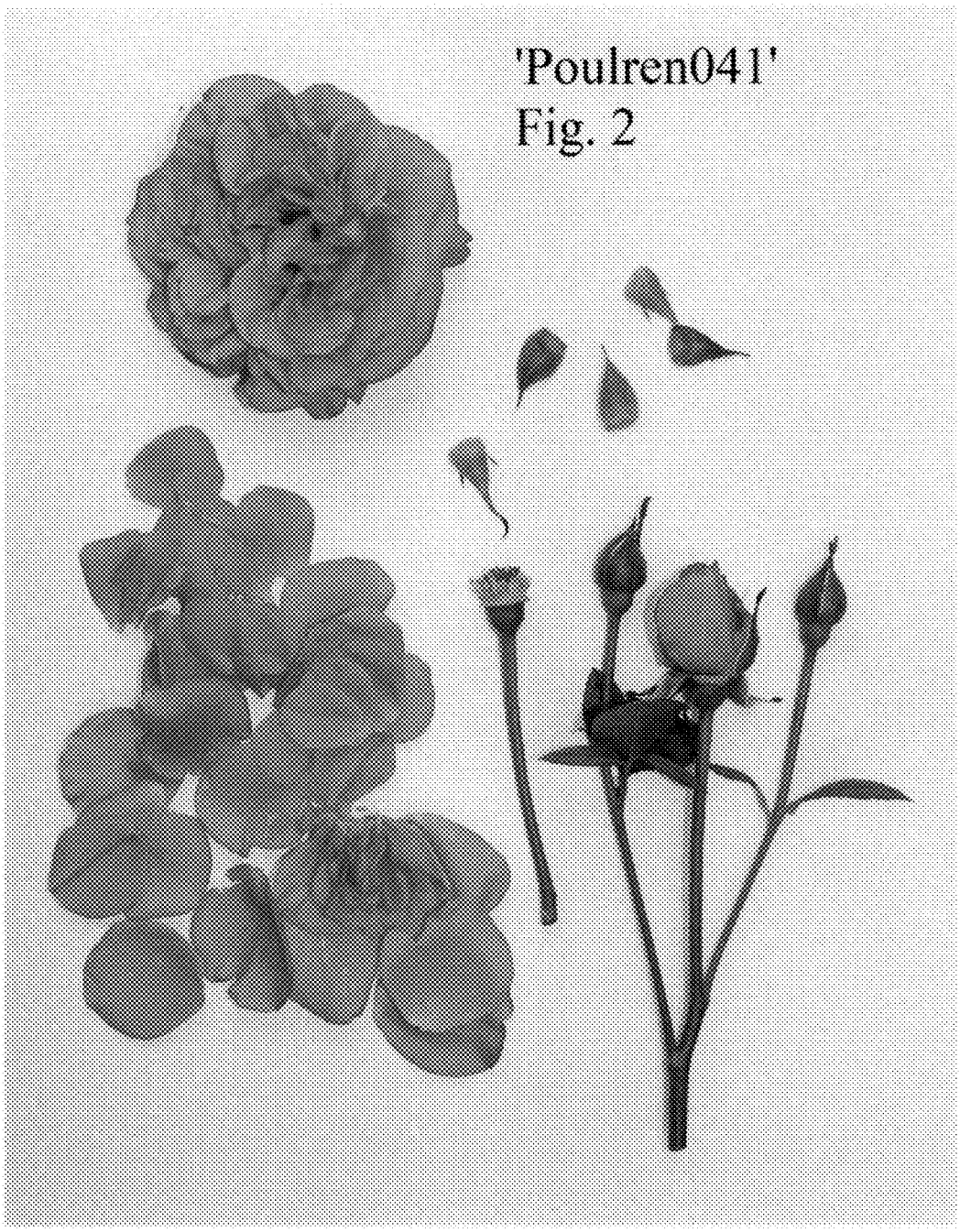

Specifically illustrated in FIG. 2 of the drawings are an open flower viewed from above, sepals detached, petals detached, reproductive flower parts, and a cluster of flower buds on the branch upon opening. Plants shown are 2 years of age.

DETAILED DESCRIPTION OF THE VARIETY

The following is a description of 'Poulren041', as observed in its growth in an outdoor nursery in Odense Denmark. Observed plants are 24 months of age, and were grown on their own roots in 35 cm pots. Color references are made using The Royal Horticultural Society (London, England) Colour Chart, 2001, except where common terms of color are used.

For a comparison, several physical characteristics of the rose variety 'Poulren022', U.S. Plant Pat. No. 26,014 are compared to 'Poulren041'. The outer petals upon opening of 'Poulren022' are—Upper surface: Red-Purple Group N66B. Lower surface: Red-Purple Group 67B. The outer petals upon opening of 'Poulren041'are—Red-Purple Group N57A with light splashes of Orange Group 29B at the middle and lower zone. There are differences in the length of internodes in that 'Poulren022' is 40 mm, while the claimed plant internodes are 65 mm.

FLOWER AND FLOWER BUD

Blooming habit: Continuous.

Flower bud:

- *Size.*—Upon opening, 30 mm in length from base of receptacle to end of bud. Bud diameter is about 18 mm.
- *Bud form.*—Ovoid.
- *Bud color.*—As sepals divide petals are Red Purple Group 61B.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Deltoid, with wide base and acute apex. Base: Flat at union with receptacle.
- *Sepal margin.*—Margins have very weak foliaceous appendages on three of the five sepals.
- *Sepal size.*—35 to 40 mm long, 10 to 12 mm wide.
- *Receptacle.*—Texture: Smooth. Size: 12 mm in height, 8 mm wide. Color: Yellow-Green Group 144A. Shape: Campanulate.
- *Pedicel.*—Surface: Smooth. Length: About 85 mm. Diameter: 3 mm on average. Color: Yellow-Green Group 144A. Strength: Very strong.
- *Peduncle.*—Length: 3 to 5 cm. Diameter: About 4 mm. Color: Yellow-Green Group 144A. Texture: Smooth.

Flower bud development: Flower buds are borne in clusters of 3 to 5 flower buds per stem or singly.

Flower bloom:

- *Fragrance.*—Strong perfume, with notes of melon and heirloom roses.
- *Duration.*—The blooms have a duration on the plant of approximately 18 days. Petals fall cleanly away from plant after flowers have fully matured.
- *Size.*—Flower diameter is 95 mm when open. Flower depth is 50 mm.
- *Flower shape.*—Quartered-rosette. Very double flower with overlapping petals packed into quarter sections.
- *Shape of flower, side view.*—The upper portion is convex. The lower portion is concave.

Petalage: Flowers have about 90 petals.

General tonality of flower: Open flowers are Red Purple N57C with other intonations of Red-Purple Group N57B.

Petal color:

- *Upon opening, outer petals.*—Upper surface: Red-Purple Group N57A with light splashes of Orange Group 29B at the middle and lower zone. Small basal petal spot at the point of attachment Yellow Group 5A. Lower surface: Red-Purple Group 61D, blending with light shades of Red Group 52B at the middle and lower zone. Small basal petal spot at the point of attachment Yellow Group 5A.
- *Upon opening, inner petals.*—Upper surface: Red Group 52A. Very small basal petal spot at the point of attachment Yellow Group 5A. Lower surface: Red Group 52A. Very small basal petal spot at the point of attachment Yellow Group 5A.
- *After opening, outer and inner petals.*—Upper surface: Red-Purple Group N57C. Light intonations of Red-Purple Group 58D splashing at the middle and lower zone. Small basal petal spot Yellow Group 5A. Lower surface: Red-Purple Group N57C. Light intonations of Red-Purple Group 58D splashing at the middle and lower zone. Very small basal petal spot Yellow Group 5A.

Petals:

- *Petal reflex.*—Half-reflexed to 90 degrees.
- *Margin.*—Entire and uniform, very light undulation, occasional cleft.
- *Shape.*—Broad and elliptic. Apex shape: Rounded. Base shape: Acute.
- *Size.*—45 mm (l)×45 mm (w).
- *Texture.*—Soft.
- *Thickness.*—Average.

Petaloids:

- *Size.*—25 mm (l) by 10 mm (w).
- *Quantity.*—About 18.
- *Shape.*—Elliptical, not uniform, generally with a rounded base and acute apex.
- *Color.*—Red Group 52A on both sides, with basal petal spot of Yellow Group 5A.

Reproductive flower parts:

- *Pollen.*—None observed.
- *Anthers.*—Size: 2 mm in length. Color: Greyed-Orange Group 163B. Quantity: 60 on average.
- *Filaments.*—Color: Yellow-Orange Group 14B. Length: 5 mm.
- *Pistils.*—Length: 7 mm. Quantity: 35 on average.
- *Stigmas.*—Color: Orange-White Group 159D.
- *Styles.*—Color: Red-Purple Group 60A.
- *Location of stigmas.*—Superior in location relative to the length of the filaments and the height of the anthers.
- *Hips.*—None Observed.

PLANT

Plant growth: Upright, and wide. Plants are 85 cm in height, and 70 cm wide.

Stems:

- *Color of juvenile growth.*—Yellow-Green Group 144B.

*Color of mature growth*.—Yellow-Green Group 146A.

*Length*.—Canes are about 55 cm from the base of the plant to the flowering portion.

*Diameter*.—About 6 mm.

*Internodes*.—On mature canes about 65 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 9 mm.

*Shape*.—Upper portion is linear. Lower portion is deeply concave.

*Color*.—Juvenile prickles: Yellow-Green Group 144B. Mature prickles: Greyed-Purple 187A.

Plant foliage:

*Compound leaf*.—150 mm (l)×120 (w).

*Quantity*.—2 leaves per 10 cm of stem on average.

*Leaf bearing angle to the stem*.—90 degrees.

*Color of juvenile foliage*.—Upper side: Yellow-Green Group 146A with intonations of Greyed-Purple Group 183B. Lower side: Yellow-Green Group 146B with intonations of Greyed-Purple Group 183B.

Color of mature foliage.—Upper side: Yellow-Green Group 147A. Lower side: Yellow-Green Group 147B.

Plant leaves and leaflets:

*Stipules*.—Size: 13 mm long, 2 mm wide. Quantity: 2 per compound leaf. Shape: Linear, slightly broad based with outward extending apices. Margins: Finely serrated. Color:

*Petiole*.—Length: 35 to 40 mm. Diameter: 2 mm. Upper surface color: Yellow-Green Group 144A. Lower surface color: Yellow-Green Group 144A.

*Rachis*.—Length: 61 mm. Upper surface color: Yellow-Green Group 146A with intonations of Greyed-Purple Group 183B. Lower surface color: Yellow-Green Group 144A.

*Leaflet*.—Quantity: Normally 5 leaflets. Margins: Serrated. Undulations absent. Size: Terminal leaflets are about 65 to 70 mm long, 45 to 50 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren041' substantially as described and illustrated herein.

* * * * *

'Poulren041'

'Poulren041'